United States Patent [19]
Markert

[11] Patent Number: 6,028,231
[45] Date of Patent: Feb. 22, 2000

[54] PROCESS FOR PREPARING 2-METHYL-4-(2, 2,3-TRIMETHYL-CYCLOPENT-3-EN-1-YL)-BUT-2-EN-1-OL

[75] Inventor: Thomas Markert, Monheim, Germany

[73] Assignee: Henkel Kommanditgesellschaft auf Aktien, Duesseldorf, Germany

[21] Appl. No.: 09/284,790

[22] PCT Filed: Oct. 15, 1997

[86] PCT No.: PCT/EP97/05689

§ 371 Date: Apr. 20, 1999

§ 102(e) Date: Apr. 20, 1999

[87] PCT Pub. No.: WO98/17613

PCT Pub. Date: Apr. 30, 1998

[30] Foreign Application Priority Data

Oct. 24, 1996 [DE] Germany ............ 196 44 250

[51] Int. Cl.⁷ ................................. C07C 35/06
[52] U.S. Cl. ............................................. 568/838
[58] Field of Search ............................... 568/838

[56] References Cited

U.S. PATENT DOCUMENTS 5,874,649 2/1999 Tanaka .................... 568/838

FOREIGN PATENT DOCUMENTS 19 22 391   8/1970   Germany .
55-036423   3/1980   Japan .
55-39330   10/1980   Japan .

OTHER PUBLICATIONS

E.T.Morris, Dragoco Report, vol.30 (1983) pp. 40–47 (No translation).

Flavors and Fragrances:A World Perspective, Elsevier Publishers (1988) (Title page only).

Chemical Abstracts, vol.93, No.9 (1980) p. 607.

Tetrahedron Letters, vol.36, No.20 (1995) pp.3571–3572.

Tetrahedron Letters, vol.36, No.28 (1995) pp. 5085–5088.

Chemical Abstracts, vol.94, No.15 (1981) p. 648.

*Primary Examiner*—Michael L. Shippen
*Attorney, Agent, or Firm*—Ernest G. Szoke; Wayne C. Jaeschke; Glenn E.J. Murphy

[57] ABSTRACT

A process to obtain 2-methyl-4-(2, 2, 3-trimethyl-cyclopent-3-en-1-yl)-but-2-en-1-ol by reacting campholene aldehyde and propionaldehyde via aldol condensation and further subjecting the resulting reaction mixture to Meerwein-Ponndorf reduction with aluminum alcoholates in the presence of a basic amine compound.

14 Claims, No Drawings

PROCESS FOR PREPARING 2-METHYL-4-(2,2,3-TRIMETHYL-CYCLOPENT-3-EN-1-YL)-BUT-2-EN-1-OL

FIELD OF THE INVENTION

This invention relates to an improved process for the production of the sandalwood fragrance 2-methyl-4-(2,2,3-trimethylcyclopent-3-en-1-yl)-but-2-en-1-ol by Meerwein-Ponndorf reduction of the corresponding aldehyde precursor in the presence of basic amine compounds.

DISCUSSION OF THE RELATED ART

Judging by demand, the availability of many natural fragrances is totally inadequate. From the perfumistic point of view, sandalwood oil is rated particularly highly and is of great value. It is obtained by steam distillation from the heartwood of the sandalwood tree, a tropical semiparasite which occurs in India and Malaysia. Heartwood appears after about 10 years and only begins to develop relatively quickly in 20-year-old trees. Fully grown trees are uprooted at the age of 30 to 60 because the roots are particularly rich in fragrant heartwood [cf. E. T. Morris, Dragoco Report 1983 (30), 40]. It will therefore be appreciated why fragrance researchers are constantly endeavoring to develop suitable substitutes for natural sandalwood oil.

The focal points in the development of suitable substitutes for natural sandalwood oil were outlined by R. E. Naipawer in a review [in: B. M. Lawrence, B. D. Mookherjee, B. J. Willis (Eds.): "Flavors and Fragrances: A World Perspective", Elsevier Publishers, Amsterdam 1988]. In this review, it is mentioned inter alia that, since the middle of the seventies, campholenyl derivatives have played an important part as synthetic fragrances with a sandalwood perfume. A key role in this access to synthetic sandalwood fragrances has been played by the fact that campholene aldehyde (B), the synthesis building block on which the compounds mentioned are based, can readily be obtained from α-pinene, a natural substance.

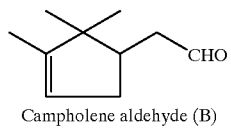

Campholene aldehyde (B)

2-Methyl4-(2,2,3-trimethylcyclopent-3-en-1-yl)-but-2-en-1-ol, hereinafter referred to in short as "sandalol" (A), is a sought-after fragrance with a pronounced sandalwood perfume. Sandalol has the following structural formula:

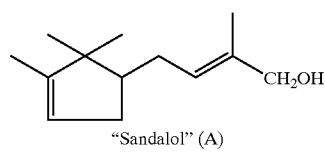

"Sandalol" (A)

Sandalol has been known to the expert for some time. Thus, DE-A-19 22 391 teaches that sandalol is obtained by initially subjecting campholene aldehyde to an aldol condensation with propionaldehyde in the presence of strongly basic catalysts, such as alkali metal alcoholates or alkali metal hydroxides, and reducing the $R_s,^{MD}$—unsaturated aldehyde obtained to the corresponding alcohol—the sandalol—in a subsequent step. The reduction may be carried out with complex metal hydrides (for example lithium aluminium hydride) or with aluminium alcoholates by the traditional Meerwein Pondorf method.

JP-A2-55/036423 (cf. Chem. Abstr. 93/094886p) describes a special process for the production of sandalol. In this process, campholene aldehyde (B) is initially reacted with propionaldehyde in the presence of sodium hydroxide as basic catalyst very much in accordance with the teaching of DE-A-19 22 391. The $R_s,^{MD}$—unsaturated aldehyde (C) formed in this mixed aldol condensation was isolated in a yield of 73.5%.

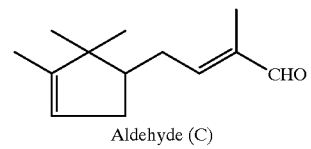

Aldehyde (C)

Finally, in another step, this unsaturated aldehyde (C) was reduced with $Al[OCH(CH_3)_2]_3$ to form the corresponding sandalol (A) in a yield said to amount to 85%.

It is known from the more recent literature that acidic auxiliary reagents, such as trifluoroacetic acid, are capable of accelerating the traditional Meerwein-Ponndorf reduction of carbonyl compounds with aluminium alcohols, cf. for example Tetrahedron Letters 1995, 36 (20), 3571—3572 and 1995, 36 (28), 5085–5088.

DESCRIPTION OF THE INVENTION

Unfortunately, the process for the production of sandalol (A) known from JP-A2-55/036423 is not entirely satisfactory in terms of yield and economy. Accordingly, there was a need for an improved process for producing the compounds (A).

It has now surprisingly been found that "sandalol" (A)

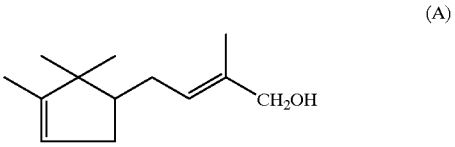

can be obtained in high yields by initially subjecting campholene aldehyde and propionaldehyde to an aldol condensation in the usual way and subsequently subjecting the reaction mixture obtained, which mainly contains the aldehyde (C)

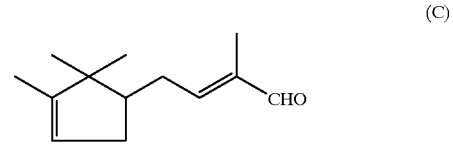

to Meerwein-Ponndorf reduction with aluminium alcoholates, this reduction step being carried out in the presence of basic amine compounds.

Accordingly, the present invention relates to a process for the production of 2-methyl4-(2,2,3-trimethylcyclopent-3-en-1-yl)-but-2-en-1-ol (A):

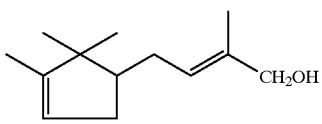

in which campholene aldehyde and propionaldehyde are conventionally reacted with one another in an aldol condensation and the reaction mixture obtained, which mainly contains the aldehyde (C):

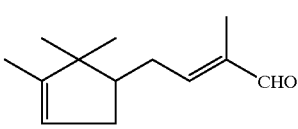

is then subjected to Meerwein-Ponndorf reduction with aluminium alcoholates, this reduction step being carried out in the presence of basic amine compounds.

The process according to the invention has the advantage over the prior art that intermediate products and end products are obtained in highly pure form and in substantially quantitative yields.

The aldol condensation, i.e. the first step of the sandalol synthesis, may be carried out in inert organic solvents. Non-polar solvents which form an azeotrope with water are particularly suitable for this purpose. Examples of suitable solvents are toluene, xylene, benzene, cyclohexane and methyl cyclohexane.

In one special embodiment of the invention, ammonium salts of an organic acid are used to catalyze the aldol condensation. Basically, the nature of the acid is not critical. Whether the ammonium salt is used as such or whether it is formed in situ during the reaction, for example from an amine and an organic acid, is not an important factor either. Examples of suitable ammonium salts are: benzyl trimethyl ammonium hydroxide, piperidinyl acetate, pyrrolidinium acetate, ammonium acetate, dimethyl ammonium pyridinyl acetate, morpholine acetate, Lewatit M600 aminopolystyrol from Bayer AG (activated with acetic acid), piperidinyl formate, N,N-tetraacetyl ethylenediamine, N,N-diacetyl ethylenediamine, dibutyl ammonium acetate and piperidinyl propionate. The concentration of the catalyst is preferably in the range from 0.001 to 20 mole-% and more preferably in the range from 0.5 to 10 mole-%, based on campholene aldehyde (B).

Propionaldehyde is preferably used in a 2.5- to 10-molar excess, based on campholene aldehyde (B). In one particular embodiment, propionaldehyde is used in a 2.5- to 3.5-molar excess.

The process according to the invention may be carried out at temperatures of 20 to 150° C. In one particularly preferred embodiment, a reaction temperature of 40 to 120° C. is adjusted.

In the second step of the sandalol synthesis, the Meerwein-Ponndorf reduction with aluminium alcoholates is carried out in the presence of basic amine compounds. It is particularly preferred to use aluminium isopropylate and/or butylate.

Examples of suitable basic amine compounds are alkyl, dialkyl and trialkyl amines, ethanolamines and diamines, pyrroles, pyrrolidines and piperidines. It has been found that the quantity of aluminium alcoholate can be distinctly reduced by the presence of the amines which are preferably used in quantities of 0.001 to 0.5 mole per mole of the aldehyde (C) to be reduced. Whereas aluminium alcoholates are normally used in quantities of more than 0.2 mole (based on the aldehyde to be reduced) in the Meerwein-Ponndorf reduction, quantities of less than 0.1 mole (based on the aldehyde to be reduced) of aluminium alcoholate are sufficient in the process according to the present invention.

The process according to the invention also has the following advantages: improved yields, easier separation of the aluminium alcoholates and greater purity of the product.

The following Examples are intended to illustrate the invention without limiting it in any way.

EXAMPLES

1. Substances used
   1.1. for the alcohol condensation
   α-campholene aldehyde:85% (Glidco)
   propionaldehyde:98% (Riedel-de Häen)
   1.2. for the reduction of the unsaturated aldehyde
   aluminium triisopropylate:aluminium propanolate (>98%), Fluka AG
2. Carrying out the reactions
   2.1. Aldol condensation

Example 1

In a 2-liter three-necked flask, 12 g of sodium lumps were gradually dissolved while stirring in 500 ml of anhydrous methanol and the resulting solution was cooled with an ice bath to around 15° C. A mixture of 152 g (0.85 mole) of α-campholene aldehyde, 72.5 g (1.25 mole) of propionaldehyde and 50 ml of methanol was then added under nitrogen from a dropping funnel over a period of 1.5 hours with stirring at a temperature of 18° C. (internal temperature). This was followed by stirring for another 1.5 hours. After a reaction time of 3 hours, the pH of the mixture was 12.9. The mixture was then neutralized with ca. 50 ml of concentrated HCl while stirring and cooling with ice water.

For working up, the mixture was extracted twice with 500 ml of petroleum ether (40:60) and the combined organic phases were washed twice with 200 ml of demineralized water, dried overnight over sodium sulfate and, after filtration, concentrated in a rotary evaporator. The yield amounted to 175 g. Analysis by gas chromatography revealed the following composition (%-area): 17.3% campholene aldehyde, 5.1% free propionaldehyde and 50.0% aldol condensation product. The percentage content of this aldol condensation product in the mixture was subsequently increased to >85% by fractionation in a high vacuum using a Vigreux column.

2.2. Reduction

In a 2-liter three-necked flask with a distillation head, 408 g (ca. 2 moles) of unsaturated aldehyde from the aldol condensation (purity>85%) were added over a period of 1 hour under nitrogen to a mixture of 41 g (ca. 0.2 mole) of aluminium triisopropylate, 6 g of diisopropyl amine and 600 g of anhydrous isopropanol, the addition being made with vigorous stirring at a boiling temperature of ca. 70° C. A mixture of acetone, isopropanol and diisopropyl amine was continuously distilled off and was periodically replaced by additions of 300 g of fresh anhydrous isopropanol. After a reaction time of 8 hours, no more acetone could be precipitated via the phenol hydrazone in the distillate. The solvent mixture was distilled off overhead and the residue was cooled to room temperature.

For working up, the product mixture was freed from aluminium salts by washing twice with 500 ml of 10% caustic soda lye at temperatures of 50 to 70° C. in order to improve phase separation. This was followed by washing twice with 500 ml of demineralized water. The crude organic phase was subjected as such to fractionation which was carried out in a high vacuum in a spinning band column. The main runnings were characterized by gas chromatography (%-area): 90.5% sandalol (A); 4.7% educt; 2.9% secondary products.

I claim:

1. A process to obtain 2-methyl-4-(2, 2, 3-trimethyl-cyclopent-3-en-1-yl)-but-2-en-1-ol of the formula (A)

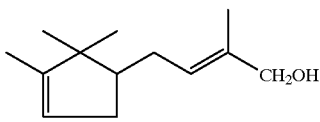

(A)

by reacting compholene aldehyde and propionaldehyde via aldol condensation to form a reaction mixture comprising an aldehyde of the formula (C):

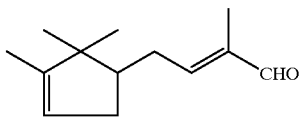

(C)

and further reacting the reaction mixture with an aluminum alcoholate via Meerwein-Ponndorf reduction in the presence of a basic amine compound.

2. A process according to claim 1, wherein the aldol condensation is carried out in an inert organic solvent.

3. A process according to claim 2, wherein the solvent is nonpolar and forms an accotrope with water.

4. A process according to claim 3, wherein the solvent is selected from the group consisting of toluene, xylene, benzene, cyclohexane, and methyl cyclohexane.

5. A process according to claim 1, wherein the aldol condensation is carried out in the presence of an ammonium salt of an organic acid.

6. A process according to claim 5, wherein the amount of ammonium salt is 0.001 to 20 mole percent based on the amount of campholene aldehyde.

7. A process according to claim 6, wherein the amount of ammonium salt is 0.5 to 10 mole percent based on the amount of campholene aldehyde.

8. A process according to claim 5, wherein the ammonium salt is selected from the group consisting of benzyl trimethyl ammonium hydroxide, piperidinyl acetate, pyrrolidinium acetate, ammonium acetate, dimethyl ammonium pyridinyl acetate, morpholine acetate, piperidinyl formate, N,N-tetraacetyl ethylene diamine, N,N-diacetyl ethylenediamine, dibutyl ammonium acetate aminopolystyrol, and piperidinyl propionate.

9. A process according to claim 1, wherein the amount of propionaldehyde is a 2.5 to 20 molar excess based on the amount of campholene aldehyde.

10. A process according to claim 1, which is carried out at 20° C. to 150° C.

11. A process according to claim 10, which is carried out at 40° C. to 120° C.

12. A process according to claim 11, wherein the aluminum alcoholate is aluminum isopropylate, aluminum butylate, or a mixture thereof.

13. A process according to claim 1, wherein the amount of basic amine compound is 0.001 to 0.5 moles per mole of aldehyde (C).

14. A process according to claim 1, wherein the basic amine compound is selected from the group consisting of alkyl, dialkyl, and trialkyl amines, ethanolamines, and diamines, pyrroles, pyrrolidines, and piperidines.

* * * * *